US006210438B1

(12) United States Patent
Sheets, Jr. et al.

(10) Patent No.: US 6,210,438 B1
(45) Date of Patent: Apr. 3, 2001

(54) BICOMPOSITE INTRAOCULAR LENS AND METHOD FOR ITS PREPARATION

(75) Inventors: John W. Sheets, Jr.; Albert R. Leboeuf, both of Fort Worth; Anilbhai S. Patel, Arlington; Mutlu Karakelle; Stephen J. Van Noy, both of Fort Worth, all of TX (US)

(73) Assignee: Alcon Laboratories, Inc., Fort Worth, TX (US)

( * ) Notice: Subject to any disclaimer, the term of this patent is extended or adjusted under 35 U.S.C. 154(b) by 0 days.

(21) Appl. No.: 09/283,670

(22) Filed: Apr. 1, 1999

Related U.S. Application Data
(60) Provisional application No. 60/081,843, filed on Apr. 15, 1998.

(51) Int. Cl.$^7$ ........................................... A61F 2/16
(52) U.S. Cl. ................................ 623/6.56; 523/106
(58) Field of Search .................. 623/5.16, 6.56, 623/924, 926; 351/160 H; 523/106, 107; 424/427

(56) References Cited

U.S. PATENT DOCUMENTS

| | | | |
|---|---|---|---|
| 4,515,794 | 5/1985 | Emery et al. ................ | 514/249 |
| 4,725,276 | 2/1988 | Bissonette et al. ............ | 623/6 |
| 4,846,833 | 7/1989 | Cumming ..................... | 623/6 |
| 4,918,165 | 4/1990 | Soll et al. ...................... | 530/391 |
| 4,950,290 | 8/1990 | Kamerling .................... | 623/6 |
| 5,002,571 | 3/1991 | O'Donnell, Jr. et al. ..... | 623/6 |
| 5,007,928 * | 4/1991 | Okamura ...................... | 623/6 |
| 5,057,578 | 10/1991 | Spinelli ......................... | 525/278 |
| 5,071,244 * | 12/1991 | Ross ............................. | 351/161 |
| 5,078,740 | 1/1992 | Walman ......................... | 623/36 |
| 5,288,293 * | 2/1994 | O'Donnell Jr. ............... | 623/6 |
| 5,290,892 | 3/1994 | Namdaran et al. ............ | 526/259 |
| 5,331,073 | 7/1994 | Weinschenk, III et al. ... | 526/264 |
| 5,358,520 | 10/1994 | Patel ............................. | 623/6 |
| 5,359,021 | 10/1994 | Weinschenk, III et al. ... | 526/264 |
| 5,366,501 * | 11/1994 | Langerman ................... | 623/6 |
| 5,370,687 * | 12/1994 | Poler ............................ | 623/6 |
| 5,371,147 * | 12/1994 | Spinelli et al. ................ | 525/288 |
| 5,375,611 * | 12/1994 | Lindqvist et al. ............. | 128/898 |
| 5,405,385 * | 4/1995 | Heimke et al. ................ | 623/6 |
| 5,494,946 * | 2/1996 | Christ et al. .................. | 523/113 |
| 5,519,069 * | 5/1996 | Burke et al. ................... | 523/106 |
| 5,549,670 * | 8/1996 | Young et al. .................. | 623/6 |
| 5,576,345 * | 11/1996 | Mansson et al. .............. | 514/449 |
| 5,593,438 * | 1/1997 | Akhavi et al. ................. | 623/6 |
| 5,628,794 | 5/1997 | Lindstrom ..................... | 623/5 |
| 5,693,094 * | 12/1997 | Young et al. .................. | 623/6 |
| 5,733,276 * | 3/1998 | Belkin ........................... | 606/6 |
| 5,869,549 | 2/1999 | Christ et al. .................. | 523/212 |
| 5,876,438 | 3/1999 | Kelleher et al. .............. | 623/4 |
| 6,027,531 | 2/2000 | Tassignon .................... | 623/6 |

FOREIGN PATENT DOCUMENTS

| | | |
|---|---|---|
| 0 559 820 B1 | 9/1993 | (EP) . |
| 0 611 379 B1 | 5/1996 | (EP) . |
| 0 781 777 A1 | 7/1997 | (EP) . |
| 0 675 910 B1 | 9/1997 | (EP) . |
| 0 904 747 A2 | 3/1999 | (EP) . |
| 0 916 320 A2 | 5/1999 | (EP) . |
| 2243612A | 11/1991 | (GB) . |
| WO 94/11764 | 5/1994 | (WO) . |
| WO 96/25962 * | 8/1996 | (WO) . |
| WO 96/34629 * | 11/1996 | (WO) . |
| WO 97/20851 * | 6/1997 | (WO) . |
| WO 97/24382 | 7/1997 | (WO) . |
| WO 98/15238 * | 4/1998 | (WO) . |
| 99/62435 | 12/1999 | (WO) . |

OTHER PUBLICATIONS

Boulton et al., "Adhesion of IOLs to the posterior capsule," *British Journal of Ophthalmology*, vol. 82(5); p. 468 (1998).
Linnola et al., "Adhesion of soluble fibronectin, laminin, and collagen type IV to intraocular lens materials," *J. of Cataract & Refractive Surgery*, vol. 25 (11), pp. 1486–1491 (1999).
Johnston et al., "In Vitro Protein Adsorption to 2 Intraocular Lens Materials," *J. Cataract & Refractive Surgery*, vol. 25, pp. 1109–1115 (1999).
Kanagawa et al., "Presence and distributio of fibronectin on the surface of implanted intraocular lenses in rabbits," *Graefe's Archive for Clinical & Exp. Ophthalmology*, vol. 228, pp. 398–400 (1990).
Linnola et al., "Intraocular lens bioactivity tested using rabbit corneal tissue cultures," *J. Cataract & Refractive Surgery*, vol. 25, pp. 1480–1485 (1999).
Liu et al., "A Study of Human Lens Cell Growth In Vitro," *Investigative Oph. & Visual Science*, vol. 37(5), pp. 906–914 (1996).
Cunanan et al., "An In Vitro Test Method to Study Posterior Capsular Opacification," *Investigative Ophthalmology & Visual Science*, vol. 38(4), p. S178 (1997).
Gabriel et al., "In Vitro Adherence of *Pseudomonas aeruginosa* to Four Intraocular Lenses," *J. Cataract Refractive Surg*, vol. 24, pp. 124–129 (1998).
Hollick et al., "Lens Epithelial Cells Regression on the Posterior Capsule: A 2 Year Prospective, Randomised Trial With Three Different IOL Materials," *Investigative Ophthalmology & Visual Science*, vol. 38(4), p. S19 (1997).
Linnola et al., "Acrylate Intraocular Lenses (IOLs) Hinder Posterior Migration of Epithelium; Activity Tested by Corneal Tissue Cultures," *ESCRS Abstracts*, p. 120 (1997).*
Linnola, "Sandwich Theory: Bioactivity–based Explanation for Posterior Capsule Opacification," *J. Cataract Refract. Surg.*, vol. 23, pp. 1539–1542 (1997).*

(List continued on next page.)

*Primary Examiner*—Paul B. Prebilic
(74) *Attorney, Agent, or Firm*—Patrick M. Ryan

(57) ABSTRACT

Bicomposite intraocular lenses having an anterior surface material different from a posterior surface material are disclosed. The posterior surface material reduces the risk of posterior capsule opacification.

16 Claims, No Drawings

OTHER PUBLICATIONS

Mandle, "Acrylic Lenses Cause Less Posterior Capsule Opacification than PMMA, Silicone IOLs," *Ocular Surgery News*, vol. 14(15), p. 23 (1996).*

Nagamoto et al., "Effect of Intraocular Lens Design on Migration of Lens Epithelial Cells Onto the Posterior Capsule," *J. Cataract Refract Surg.*, vol. 23, pp. 866–872 (1997).

Nagata et al., "Adhesiveness of AcrySof to a Collagen Film," *J. Cataract Refract. Surg.*, vol. 24, pp. 367–370 (1998).

Nagata et al., "Optic Sharp Edge or Convexity: Comparison of Effects of Posterior Capsular Opacification," *Jpn J. Ophthal.*, vol. 40, pp. 397–403 (1996).

Nishi et al., Inhibition of Migrating Lens Epithelial Cells By Blocking The Adhesion Molecule Integrin: A Preliminary Report, *J. Cataract Refract. Surg*, vol. 23 (1997).

Oshika et al., "Adhesion of Lens Capsule to Intraocular Lenses of Polymethylmethacrylate, Silicone and Acrylic Foldable Materials: An Experimental Study," *British Journal of Ophthalmology*, vol. 82, pp. 549–553 (1998).

Oshika et al., "Incision/Phacoemulsification," Symposium on Cataract, IOL and Refractive Surgery, Jun., 1996.

Oshika et al., "Two Year Clinical Study of a Soft Acrylic Intraocular Lens," *J. Cataract Refract. Surg.*, vol. 22, pp. 104–109 (1996).

Pande et al., "High–Resolution Digital Retroillumination Imaging of the Posterior Lens Capsule After Cataract Surgery," *J. Cataract Refract. Surg.*, vol. 23, pp. 1521–1527 (1997).

Pande et al., "Posterior Capsular Opacfication With PMMA, Silicone and Acrysof Intraocular Lenses: A Prospective Randomized Clinical Trial," *Investigative Ophthalmology & Visual Science*, vol. 36(4), p. S397 (1995).

Reich et al., "Intraocular–Lens–Endothelial Interface: Adhesive Force Measurements," *J. of Biomedical Materials Research*, vol. 18, pp. 737–744 (1984).

Saika et al., "Cell Proliferation on the Outer Anterior Capsule Surface After Extracapsular Lens Extraction in Rabbits," *J. Cataract Refractive Surg.* vol. 23, pp. 1528–1531 (1997).

Ursell et al., Anterior Capsule Stability in Eyes With Intraocular Lenses Made of Poly(methyl methacrylate), Silicone, and AcrySof, .*J. Cataract Refractive Surg.*, vol. 23, pp. 1532–1538 (1997).

Ursell et al., "Relationship Between Intraocular Lens Biomaterials and Posterior Capsule Opacification," *J. Cataract Refractive Surg.* vol. 24, pp. 352–360 (1998).

Ursell et al., "The In Vivo Movement of Cells on the Surface of Intraocular Lenses in Humans Observed with Sequential Specular Photomicrography," *Investigative Ophthalmology & Visual Science*, vol. 36(4), S795 (1995).

Werner et al., "Endothelial Damage Caused by Uncoated and Fluorocarbon–Coated Poly(methyl methacrylate) Intraocular Lenses," *J. Cataract Refractive Surgery*, vol. 23, pp. 1013–1019 (1997).

Yang et al., "Membrane Formation and Cellular Response on the Surface of Lenses Implanted in Rabbit Eyes," *J. Cataract Refractive Surg.*, vol. 23, pp. 1265–1270 (1997).

* cited by examiner

BICOMPOSITE INTRAOCULAR LENS AND METHOD FOR ITS PREPARATION

This application claims priority from co-pending U.S. Provisional Patent Application Serial No. 60/081,843, filed Apr. 15, 1998.

FIELD OF THE INVENTION

This invention relates to intraocular lenses. In particular, the present invention relates to a method of preparing a bicomposite intraocular lens material comprising a posterior surface for reducing the risk of posterior capsule opacification.

BACKGROUND OF THE INVENTION

Foldable intraocular lens ("IOL") materials can generally be divided into three categories: silicone materials, hydrogel materials, and non-hydrogel acrylic materials. Many materials in each category are known. See, for example, *Foldable Intraocular Lenses*, Ed. Martin et al., Slack Incorporated, Thorofare, N.J. (1993). Biocompatibility varies among different IOL materials within and among each category.

One measure of biocompatability for an IOL can be the incidence of posterior capsule opacification ("PCO"). A number or factors may be involved in causing and/or controlling PCO. For example, the design and edge sharpness of an IOL may be a factor. See, Nagamoto et al., J. Cataract Refract. Surg., 23:866–872 (1997); and Nagata et al., Jpn. J. Ophthalmol., 40:397–403 (1996). See, also, U.S. Pat. Nos. 5,549,670 and 5,693,094. Another factor appears to be the lens material itself. See, for example, Mandle, "Acrylic lenses cause less posterior capsule opacification than PMMA, silicone IOLs," Ocular Surgery News, Vol. 14. No. 15, p. 23 (1996). See, also, Oshika, et al., "Two Year Clinical Study of a Soft Acrylic Intraocular Lens, " J. Cataract. Refract. Surg., 22:104–109 (1996); and Ursell et al., "Relationship Between Intraocular Lens Biomaterials and Posterior Capsule Opacification, " J. Cataract Refract. Surg., 24:352–360 (1998).

One method of addressing the PCO problem involves administering a pharmaceutical agent to the capsular bag area at the time of, or immediately after, extracapsular cataract extraction. See, for example, U.S. Pat. No. 5,576,345 (pharmaceutical agent=the cytotoxic agent taxol or an ophthalmically acceptable derivative); U.S. Pat. No. 4,515,794; and U.S. Pat. No. 5,370,687. Alternatively, the pharmaceutical agent may be tethered to the surface of the IOL material. See, for example, U.S. Pat. No. 4,918,165. The pharmaceutical agents are intended to kill or prevent the growth of proliferating cells that might cause PCO or "secondary cataracts. " Yet another method involves the physical destruction or removal of lens epithelial cells. See, Saika et al., J. Cataract Refract. Surg., 23:1528–1531 (1997).

Another method of addressing PCO is the prophylactic laser therapy method disclosed in U.S. Pat. No. 5,733,276. According to this method, the lens capsule is irradiated with laser irradiation to destroy cells which remain in the lens capsule after extraction of a cataract.

Other methods theorized for reducing the risk of PCO involve adhering the posterior capsule to the IOL at the time of implantation, as in U.S. Pat. No. 5,002,571. According to the '571 patent, a non-biological glue or, preferably, a biological glue, such as fibrin, collagen, or mussel glue, is used to adhere the posterior lens capsule to the posterior surface of an IOL. The glue may be applied over the entire posterior surface of the IOL or just as an annulus around the outer perimeter of the posterior surface of the IOL.

In contrast, U.S. Pat. No. 5,375,611 discloses a method of reducing the risk of PCO by preventing the adherence of the posterior capsule to the IOL. According to the '611 patent, the posterior surface of the lens capsule itself is chemically modified at the time of extracapsular cataract extraction. The chemical modification is achieved by depositing a water-insoluble stable or permanent layer of a cell attachment preventing compound onto the posterior surface of the lens capsule. The stable or permanent layer may be a polymer, such as polyethylene glycol, polysaccharides, polyethylenepropylene glycol, and polyvinyl alcohols.

SUMMARY OF THE INVENTION

The present invention relates to a bicomposite intraocular lens and a method for its preparation. According to the present invention, a bicomposite IOL optic comprising an anterior surface material consisting of an ophthalmically acceptable lens-forming material and a posterior surface material, different from the anterior surface material, for reducing the risk of posterior capsule opacification is prepared. The posterior surface material consists essentially of two or more aryl acrylic hydrophobic monomers. The method comprises the steps of (a) forming a posterior surface layer of material by polymerizing a posterior surface material composition consisting essentially of two or more aryl acrylic hydrophobic monomers and a cross-linking agent in a mold having the desired IOL posterior surface shape; (b) forming an anterior surface layer by adding a liquid anterior composition consisting of an ophthalmically acceptable IOL material to the top of the posterior surface layer and polymerizing the liquid anterior composition.

DETAILED DESCRIPTION OF THE INVENTION

The bicomposite IOL of the present invention comprises an anterior surface layer and a posterior surface layer, different from the anterior surface layer, which reduces the risk of posterior capsule opacification.

STEP (A):

The bicomposite IOL is prepared by first polymerizing a posterior surface material consisting essentially of at least two aryl acrylic hydrophobic monomers of the formula

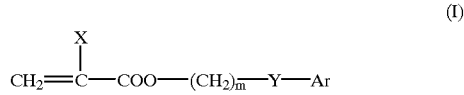

(I)

wherein: X is H or $CH_3$;

m is 0–10;

Y is nothing, O, S, or NR wherein R is H, $CH_3$, $CnH_{2n+1}$ (n=1–10) iso $OC_3H_7$, $C_6H_5$, or $CH_2C_6H_5$;

Ar is any aromatic ring which can be unsubstituted or substituted with $CH_3$, $C_2H_5$, n-$C_3H_7$, iso-$C_3H_7$, $OCH_3$, $C_6H_{11}$, Cl, Br, $C_6H_5$, or $CH_2C_6H_5$;

and a cross-linking agent.

Monomers of Formula I are known and include, but are not limited to: 2-phenoxyethyl acrylate; 2-phenylethylthio acrylate; 2-phenylethylamino acrylate; phenyl acrylate; benzyl acrylate; 2-phenylethyl acrylate; 3-phenylpropyl acrylate; 3-phenoxypropyl acrylate; 4-phenylbutyl acrylate; 4-phenoxybutyl acrylate; 4-methylphenyl acrylate; 4-methylbenzyl acrylate; 2-2-methylphenylethyl acrylate; 2-3-methylphenylethyl acrylate; 2-4-methylphenylethyl acrylate; and their corresponding methacrylate compounds.

These acrylic/methacrylic monomers and others are disclosed in U.S. Pat. No. 5,290,892, the entire contents of which are hereby incorporated by reference.

Preferred monomers of Formula I are those where m is 2–4; Y is nothing or O; and Ar is phenyl. Most preferred are 2-phenylethyl acrylate; 2-phenoxyethyl acrylate; 3-phenylpropyl acrylate; 3-phenoxypropyl acrylate; 4-phenylbutyl acrylate; 4-phenoxybutyl acrylate; and their corresponding methacrylate compounds. The posterior surface materials of the present invention preferably contain at least one monomer of Formula I that is a methacrylate monomer (X=CH$_3$) and at least one monomer of Formula I that is an acrylate monomer (X=H). Most preferred are posterior surface materials consisting essentially of at least one monomer of Formula I that is a methacrylate monomer (X=CH$_3$) and at least one monomer of Formula I that is an acrylate monomer (X=H), wherein the total amount of the acrylate monomer(s) of Formula I is greater than the total amount of methacrylate monomer(s) of Formula I. In one preferred embodiment, the IOL coating composition consists essentially of 2-phenylethyl acrylate and 2-phenylethyl methacrylate, and more preferably, about 65% (w/w) of 2-phenylethylacrylate and about 30% (w/w) of 2-phenylethyl methacrylate.

The posterior surface material also contains a cross-linking agent. The copolymerizable cross-linking agent used in the copolymers of this invention may be any terminally ethylenically unsaturated compound having more than one unsaturated group. Combinations of cross-linking monomers are also suitable. Suitable cross-linking agents include, for example: ethylene glycol dimethacrylate; diethylene glycol dimethacrylate; ethyleneglycol diacrylate; allyl methacrylate; 1,3-propanediol dimethacrylate; allyl methacrylate; allyl acrylate; 1,6-hexanediol dimethacrylate; 1,4-butanediol dimethacrylate; polyethyleneoxide diacrylates; and the like. A preferred cross-linking agent is 1,4-butanediol diacrylate (BDDA). The amount of the cross-linking agent in the posterior surface material will depend upon, among other factors, the degree of cross-linking desired. In general, however, the amount of the cross-linking agent in the posterior surface material is at least 0.1% (w/w) up to about 10% (w/w).

The posterior surface material also comprises a polymerization initiator. Suitable polymerization initiators include thermal initiators and photoinitiators. A preferred thermal initiator is di-(tert-butylcyclohexyl) peroxydicarbonate (commercially available as Perkadox® 16 from Akzo Chemicals Inc., Chicago, Ill.). Suitable photoinitiators include UV- and blue-light photoinitiators. Many such photoinitiators are known. Preferred blue-light photoinitiators are benzoylphosphine oxide initiators, such as 2,4,6-trimethyl-benzoyidiphenylophosphine oxide; bis-(2,6-dichlorobenzoyl)-4-N-propylphenyl-phosphine oxide; and bis-(2,6-dichlorobenzoyl)-4-N-butylphenyl-phosphine oxide. Most preferred are 2,4,6-trimethyl-benzoyldiphenylophosphine oxide, commercially available as Lucirin® TPO from BASF Corporation (Charlotte, N.C.) and Darocur 4265 from Ciba Geigy. See, for example, commonly-assigned, co-pending U.S. patent application Ser. No. 08/908,229, filed on Aug. 7, 1997, the entire contents of which are hereby incorporated by reference. In general, the amount of the polymerization initiator contained in the posterior surface material to be polymerized in step (a) is about 3% (w/w) or less, and preferably about 2% (w/w) or less.

In addition to the monomers of Formula I, the cross-linking agent and the polymerization initiator, the posterior surface layer optionally comprises one or more ingredients selected from the group consisting of UV absorbers and blue-light blocking colorants. If either or both types of absorbers are present, the polymerization initiator should be chosen so that there is minimal interference with initiator activation.

Ultraviolet absorbing chromophores can be any compound that absorbs light having a wavelength shorter than about 400 nm, but does not absorb any substantial amount of visible light. It is preferred to use an ultraviolet absorbing compound that is copolymerizable with the monomers of Formula I. Suitable copolymerizable ultraviolet absorbing compounds are the substituted 2-hydroxybenzophenones disclosed in U.S. Pat. No. 4,304,895 and the 2-hydroxy-5-acryloxyphenyl-2H-benzotriazoles disclosed in U.S. Pat. No. 4,528,311. The most preferred ultraviolet absorbing compound is 2-(3'-methallyl-2'-hydroxy-5'-methyl phenyl) benzotriazole ["o-Methallyl Tinuvin P"].

If a blue-light absorbing compound, e.g. a yellow dye, is included in the posterior surface material, it is preferably copolymerizable with the monomers of Formula 1. Suitable polymerizable blue-light blocking chromophores include those disclosed in U.S. Pat. No. 5,470,932.

A preferred posterior surface material consists essentially of 2-phenylethyl acrylate; 2-phenylethyl methacrylate; 1,4-butanediol diacrylate; and o-Methallyl Tinuvin P. For this preferred material, the preferred polymerization initiator is Perkadox 16. The most preferred posterior surface material consists essentially of about 65 parts by weight of 2-phenylethyl acrylate; about 30 parts by weight of 2-phenylethyl methacrylate; about 3.2 parts by weight of 1,4-butanediol diacrylate; and about 1.8 parts by weight of o-Methallyl Tinuvin P.

The posterior surface material is formed by mixing the monomers of formula (I), the cross-linking agent, the polymerization initiator, and any UV- or blue-light absorbing compounds, and polymerizing the resulting mixture in a mold having the shape desired for the posterior surface of the IOL. The mixture is polymerized by activation of the polymerization initiator. The amount of posterior surface material to be polymerized should be that amount necessary to provide a posterior surface layer of about 100 μm or less, preferably about 25 μm or less.

STEP (B):

After the posterior surface material is polymerized, the anterior surface material is prepared. The anterior surface material consists of any ophthalmically acceptable IOL material, such as silicone materials, hydrogel materials and hydrophobic acrylic materials. The anterior surface material may be a "hard" (intended to be inserted in an unfolded state) IOL material or a "foldable" (intended to be inserted in a folded or compressed state) IOL material. The anterior surface material may comprise two or more monomers of formula (I), provided only that the anterior surface material is different from the posterior surface material. For example, the anterior surface material could be an IOL material disclosed in U.S. Pat. Nos. 5,693,095 or 5,331,073. A preferred anterior surface material comprises 2-phenylethyl acrylate and 2-hydroxyethyl methacrylate. A most preferred anterior surface material comprises about 80 wt. % of 2-phenylethyl acrylate; about 15 wt. % of 2-hydroxyethyl methacrylate; about 3.2 wt. % of 1,4-butanediol diacrylate; and about 1.8 wt. % of 2-(3'-methallyl-2'-hydroxy-5'-methyl phenyl) benzotriazole.

The anterior surface material comprises a polymerization initiator. The polymerization initiator can be a thermal initiator or a radiation-activated initiator (e.g., electron beam, UV- or blue-light activated initiators). The polymerization initiator should be chosen so that the anterior surface material may be polymerized quickly after contacting the polymerized posterior surface material in order avoid allowing the anterior surface material to penetrate beyond an interfacial region of approximately 1–2 μm. In general, the liquid anterior surface material should not penetrate the posterior surface material beyond one-half of the thickness of the posterior surface material. For penetration depths beyond 1–2 μm, however, optical distortion may be significant, depending upon the identity and thickness of the posterior surface material. The anterior surface material may additionally comprise one or more ingredients selected from the group consisting of cross-linking agents, polymerization initiators, UV-absorbing compounds and blue-light absorbing compounds.

The anterior surface material is prepared by mixing the chosen anterior surface material ingredients and casting them on top of the posterior surface layer formed in step (a) in a mold having the shape desired for the anterior surface of the IOL. The anterior surface material is then polymerized, attaching to the posterior surface material by means of an interpenetrating polymer network. The curing conditions for the anterior surface material are preferably controlled to minimize the depth of the interpenetrating network.

The anterior and posterior surface materials are preferably selected so that together they form an IOL material that possesses the following refractive index, $T_g$, and elongation properties, making it particularly suitable for use as a foldable IOL.

The IOL material preferably has a refractive index of at least about 1.50 as measured by an Abbe' refractometer at 589 nm (Na light source). IOL optics made from materials having a refractive index lower than 1.50 are necessarily thicker than optics of the same power which are made from materials having a higher refractive index. As such, IOL optics made from materials having a refractive index lower than about 1.50 generally require relatively larger incisions for IOL implantation.

The glass-transition temperature ("Tg") of the IOL material, which affects the material's folding and unfolding characteristics, is preferably between about −20 to +25° C., and more preferably between about −5 and +16° C. Tg is measured by differential scanning calorimetry at 10° C./min., and is determined at the midpoint of the transition of the heat flux curve.

The IOL material should also have an elongation of at least about 150%, preferably at least 200%, and most preferably about 300–600%. This property indicates that an IOL optic made of the material generally will not crack, tear or split when folded. Elongation of polymer samples is determined on dumbbell shaped tension test specimens with a 20 mm total length, length in the grip area of 4.88 mm, overall width of 2.49 mm, 0.833 mm width of the narrow section, a fillet radius of 8.83 mm, and a thickness of 0.9 mm. Testing is performed on samples at ambient conditions using an Instron Material Tester (Model No. 4442 or equivalent) with a 50 Netwon load cell. The grip distance is set at 14 mm and a crosshead speed is set at 500 mm/minute and the sample is pulled until failure. The elongation (strain) is reported as a fraction of the displacement at failure to the original grip distance.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

We claim:

1. A bicomposite intraocular lens comprising an anterior surface material consisting of an ophthalmically acceptable lens-forming material and a posterior surface material, different from the anterior surface material, for reducing the risk of posterior capsule opacification, wherein the posterior surface material is a capplymer that consists essentially of two or more aryl acrylic hydrophobic monomers of the formula

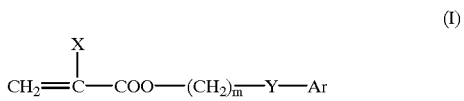

wherein: X is H or $CH_3$;
m is 0–10;
Y is nothing, O, S, or NR wherein R is H, $CH_3$, $C_nH_{2n+1}$, iso-$OC_3H_7$, $C_6H_5$, or $CH_2C_6H_5$;
n is 1–10;
Ar is any aromatic ring which can be unsubstituted or substituted with $CH_3$, $C_2H_5$, n-$C_3H_7$, iso-$C_3H_7$, $OCH_3$, $C_6H_{11}$, Cl, Br, $C_6H_6$, or $CH_2C_6H_5$;
and a cross-linking agent;
and wherein the posterior surface material optionally contains one or more ingredients selected from the group consistingq of UV, absorbers and blue-light blocking colorants.

2. The bicomposite intraocular lens of claim 1 wherein the aryl acrylic hydrophobic monomers of formula I are selected from the group consisting of 2-phenoxyethyl acrylate, 2-phenylethylthio acrylate, 2-phenylethylamino acrylate, phenyl acrylate, benzyl acrylate, 2phenylethyl acrylate, 3phenylpropyl acrylate, 3-phenoxypropyl acrylate, 4-phenylbutyl acrylate, 4-phenoxybutyl acrylate, 4-methylphenyl acrylate, 4-methylbenzyl acrylate, 2-2-methylphenylethyl acrylate, 2-4-methylphenylethyl acrylate, 2-4-methylphenylethyl acrylate, and their corresponding methcrylate compounds.

3. The bicomposite intraocular lens of claim 2 wherein the aryl acrylic hydrophobic monomers of Formula I are selected from the group consisting of 2-phenylethyl acrylate, 2-phenoxyethyl acrylate, 3-phenylpropyl acrylate, 3-phenoxypropyl acrylate, 4-phenylbutyl acryate, and 4-phenoxybutyl acrylate, and their corresponding methacrylate compounds.

4. The bicomposite intraocular lens of claim 1 wherein the aryl acrylic hydrophobic monomers of Formula I consist essentially of at least one monomer wherein X=H and at least one monomer wherein X=$CH_3$.

5. The bicomposite intraocular lens of claim 4 wherein the amount of monomer wherein X=H is greater than the amount of monomer wherein X=$CH_3$.

6. The bicomposite intraocular lens of claim 4 wherein the aryl acrylic hydrophobic monomers of Formula 1 consist essentially of 2-phenylethyl acrylate and 2-phenylethyl methacrylate.

7. The bicomposite intraocular lens of claim 1 wherein the cross-linking agent is selected from the group consisting of ethylene glycol dimethacrylate, diethylene glycol dimethacrylate, ethyleneglycol diacrylate, allyl methacrylate, 1,3-propanediol dimethacrylate, allyl methacrylate, allyl acrylate, 1,6-hexanediol dimethacrylate, 1,4-butanediol dimethacrylate, polyethyleneoxide mono- and diacrylates, and 1,4-butanediol diacrylate.

8. The bicomposite intraocular lens of claim 1 wherein the posterior surface material further comprises one or more ingredients selected from the group consisting of UV absorbers and blue-light blocking colorants.

9. The bicomposke intraocular lens of claim 1 wherein the posterior surface material consists essentially of 2-phenylethyl acrylate, 2-phenylethyl methacrylate, 1,4-butanediol diacrylat, and 2-(3'-methallyl-2'-hydroxy-5'-methyl phenyl) benzotriazole.

10. The bicomposite intraocular lens of claim 9 wherein the posterior surface material is polyerise using polymerization initiator is di-(tert-butylcyclohexyl) peroxydicarbonate.

11. The bicomposifte intraocular lens of claim 10 wherein the posterior surface material is about 100 $\mu$m or less in total thickness.

12. The bicomposite intraocular lens of claim 11 wherein the posterior surface material is about 25 $\mu$m or less in total thickness.

13. A method of preparing a bicomposite intraocular lens having a posterior side and an anterior side comprising the steps of
  (a) forming a posterior surface material in a mold having a shape desired for the posterior side, wherein the posterior surface material is a copolymer that consists essentially of two or more aryl acrylic hydrophobic monomers of the formula

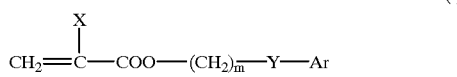

(I)

wherein: X is H or $CH_3$;

m is 0–10;

Y is nothing, O, S, or NR wherein R is H, $CH_3$, $C_nH_{2n+1}$iso-$OC_3H_7$, $C_6H_5$, or $CH_2C_6H_5$;

n is 1–10;

Ar is any aromatic ring which can be unsubstituted or substituted with $CH_3$, $C_2H_5$, n-$C_3H_7$, iso-$C_3H_7$, $OCH_3$, $C_6H_{11}$, Cl, Br, $C_6H_5$, or $CH_2C_6H_6$;

and a cross-linking agent;

and wherein the posterior surface material optonally contains one or more ingredients selected from the group consisting of UV absorbers and blue-ight blocking colorants, and (b) forming an anterior surface material by curing a liquid anterior surface composition on top of the posterior surface material, wherein the anterior surface material oonsists of an ophthalmically acceptable intraocular lens material and the anterior surface material is attached to the posterior surface material by means of an interpenetrating polymer network.

14. The method of claim 13 wherein the posterior surface material consists essentially of 2-phenylethyl acrylate and 2-phenyletyl methacrylate.

15. The method of claim 13 wherein the anterior surface material is selected from the group consisting of silicone materials, hydrogel materials, and hydrophobic acrylic materials.

16. The method of claim 15 wherein the anterior surface material comprises 2-phenylethyl acrylate and 2-hydroxyethyl methacrylate.

* * * * *